(12) United States Patent
Fernandes

(10) Patent No.: US 8,247,394 B2
(45) Date of Patent: Aug. 21, 2012

(54) METHODS OF TREATING URETHRITIS AND RELATED INFECTIONS USING FUSIDIC ACID

(75) Inventor: Prabhavathi Fernandes, Chapel Hill, NC (US)

(73) Assignee: Cempra Pharmaceuticals Inc., Chapel Hill, NC (US)

( * ) Notice: Subject to any disclaimer, the term of this patent is extended or adjusted under 35 U.S.C. 154(b) by 267 days.

(21) Appl. No.: 12/791,945

(22) Filed: Jun. 2, 2010

(65) Prior Publication Data
US 2011/0301132 A1 Dec. 8, 2011

(51) Int. Cl.
*A61K 31/56* (2006.01)
(52) U.S. Cl. ........................ 514/171; 514/182
(58) Field of Classification Search .................. 514/171, 514/182
See application file for complete search history.

(56) References Cited

U.S. PATENT DOCUMENTS

| | | | |
|---|---|---|---|
| 6,673,783 B2 * | 1/2004 | Duvold | ........................ 514/182 |
| 2002/0142948 A1 | 10/2002 | Oleson, Jr. et al. | |
| 2004/0018234 A1 | 1/2004 | Rudnic et al. | |

OTHER PUBLICATIONS

Van Bijsterveld et al. CAS:1987: 227404, 1987.*
Goldbaun et al. CAS: 64: 62413, 1966.*
Panagopoulos, P. et al, International Journal of Antimicrobial Agents, 2008, vol. 32, pp. 485-487.
MacGowan, A.P. et al, Journal of Antimicrobial Chemotherapy, 1989, vol. 23, pp. 409-415.
Taburet, A.M. et al, Journal of Antimicrobial Chemotherapy, 1990, vol. 25, Suppl. B, pp. 23-31.
Aarestrup FM ed. Antimicrobial Resistance in Bacterial of Animal Origin, ASM Press, Washington DC 2006.
Adimora, A.A., Treatment of uncomplicated genital *Chlamydia trachomatis* infections in adults. Clin. Infect. Dis. 35: Suppl S2,183-186 (2002).
Besier, S., et al., Compensatory Adaptation to the Loss of Biological Fitness Associated with Acquisition of Fusidic Acid Resistance in *Staphylococcus aureus*. Antimicrob. Agents Chemo. 49(4):1426-1431 (2005).
Bryskier, A, Fusidic Acid, Chapter 23, in Antimicrobial Agents: Antibacterials and Antifungals (Andre Bryskier, Ed., ASM Press, Washington, USA, 2005).
Burton, M.J., et al., The global burden of trachoma: a review. PLoS Negl Trop Dis. 3(10):e460 (2009).
Centers for Disease Control and Prevention. Update to CDC's sexually transmitted diseases treatment guidelines, "Fluoroquinolones no longer recommended for treatment of gonococcal infections." Morbidity Mortality Weekly Rpt. 56: 332-336 (2007).
Centers for Disease Control and Prevention. Increases in fluoroquinolone -resistant *Neisseria gonorrhoeae*—Hawaii and California, 2001. Morbidity Mortality Weekly Rpt. 51: 1041-1044 (2002).

Christiansen, K., Fusidic acid adverse drug reactions. Int'l J. Antimicrob. Agents 12:S3-S9 (1999).
Collignon, P. et al., Fusidic acid in vitro activity. Int'l J. Antimicrob. Agents 12:S45-S58 (1999).
Coutant, C., et al., Disk Diffusion Interpretive Criteria for Fusidic Acid Susceptibility Testing of *Staphylococci* by the National Committee for Clinical Laboratory Standards Method. Diagn Microbiol Infect Dis 25:9-13 (1996).
Creighton, S., et al., Co-infection with gonorrhoea and chlamydia: how much is there and what does it mean? Int. J. STD AIDS 14:109-113 (2003).
Evans, R.J., et al., Naturally-occurring fusidic acid resistance in *Staphylococci* and its linkage to other resistances. J. Clin. Path. 19:555-560 (1966).
Gemmell, C.G., et al. Guidelines for prophylaxis and treatment of methicillin-resistant *Staphylococcus aureus* (MRSA) infections in the UK. J. Antimicrobial Chemo. 57:589-608 (2006).
Godtfredsen, W., et al., Fucidin: a new orally active antibiotic. The Lancet 279: 928-931 (1962).
Hansson, S., et al., Structural Insight into Fusidic Acid Resistance and Sensitivity in EF-G. J. Mol. Biol. 348:939-949 (2005).
Howden, B.P., et al., Dumb and Dumber—The Potential Waste of a Useful Antistaphylococcal Agent: Emerging Fusidic Acid Resistance in *Staphylococcus aureus*. Clin. Infect. Disease 42:394-400 (2006).
Jensen, K.A., et al., FUCIDIN A Study on Problems of Resistance. Acta Pathol Microbiol Scand. 60:271-284 (1964).
Jones, R.N., et al., Update on Fusidic Acid (CEM-102) Tested against *Neisseria gonorrhoeae* and *Chlamydia trachomatis*. Antimicrob. Agents Chemother., 54(10): 4518-4519 (2010).
Mandell et al., Fusidic Acid, in Principles and Practice of Infectious Diseases, 6th ed. (Mandell et al. eds., Elsevier, 2006).
Merchant, R.C., et al., Adequacy of testing, empiric treatment, and referral for adult male emergency department patients with possible *Chlamydia* and/or gonorrhoea urethritis. Int. J. STD AIDS 20:534-539 (2009).
Nordin, P. et al., A comparison of fusidic acid and flucloxacillin in the treatment of skin and soft-tissue infection. Eur. J. Clin. Res. 5:97-106 (1994).
Olanrewaju et al., CEM-102 (Sodium Fusidate) dosage regimen decision support using population pharmacokinetic (PPK) and mechanism-based pharmacokinetic-pharmacodynamic (PK-PD) models. Abstr. A-1141. 47th Ann. Meet. Infec. Dis. Soc. Am. Infectious Diseases Society of America, Philadelphia, PA (2009).
Palmer, H.M., et al., Emergence and spread of azithromycin-resistant *Neisseria gonorrhoeae* in Scotland. J. Antimicrob. Chemother. 62:490-494 (2008).
Reeves, D., Review—The pharmacokinetics of fusidic acid, J. Antimicrob. Chemother. 20:467-476 (1987).

(Continued)

*Primary Examiner* — Rei-tsang Shiao
(74) *Attorney, Agent, or Firm* — Roylance, Abrams, Berdo & Goodman, L.L.P.

(57) ABSTRACT

Methods for the treatment and prevention of a bacterial infection caused by *Neisseria gonorrhoeae*, or *Chlamydia trachomatis*, or both *Neisseria gonorrhoeae* and *Chlamydia trachomatis*, such as urethritis, an ocular infection, or a pharyngeal infection, using fusidic acid, or pharmaceutically acceptable salt thereof, are described.

20 Claims, No Drawings

OTHER PUBLICATIONS

Rieutord, A., et al., In vitro study of the protein binding of fusidic acid: a contribution to the comprehension of its pharmacokinetic behaviour. Int'l J. Pharmaceutics 119:57-64 (1995).

Roberts, M.C., et al., Erythromycin-resistant *Neisseria gonorrhoeae* and oral commensal *Neisseria* spp. carry known rRNA methylase genes. Antimicrob. Agents Chemother. 43:1367-1372 (1999).

Roblin, P.M., et al., Microbiologic efficacy of azithromycin and susceptibilities to azithromycin of isolates of *Chlamydia pneumoniae* from adults and children with community-acquired pneumonia. Antimicrob. Agents Chemother. 42:194-196 (1998).

Skov, R. et al., Correlation of MIC methods and tentative interpretive criteria for disk diffusion susceptibility testing using NCCLS methodology for fusidic acid. Diag. Micro. Infect. Dis. 40:111-116 (2001).

Spelman, D., Fusidic acid in skin and soft tissue infections. Int'l J. Antimicrob. Agents 12:S59-S66 (1999).

Still, J.G., et al., Pharmacokinetics and safety of single, multiple, and loading doses of CEM-102 in healthy subjects, abstr. A1-1931. 49th Intersci. Conf. Antimicrob. Agents and Chemother., San Francisco, CA (Sep. 12-15, 2009).

Turnidge, J., Fusidic acid pharmacology, pharmacokinetics and pharmacodynamics. Int'l J. Antimicro.I Agents 12:S23-S34 (1999).

Van Bijsterveld, O.P., et al., Fusidic Acid in Infections of the External Eye. Infection 15:16-20 (1987).

Verbist, L., The antimicrobial activity of fusidic acid. J. Antimicro. Chemother. 25, Suppl. B, 1-5 (1990).

Von Daehne et al., Adv. Applied Microbiol. 25:95-146 (1979).

\* cited by examiner

METHODS OF TREATING URETHRITIS AND RELATED INFECTIONS USING FUSIDIC ACID

BACKGROUND OF THE INVENTION

Urethritis is an inflammation of the urethra in men and women, commonly caused by a bacterial infection and considered to be a sexually transmitted disease. Two main forms of bacterial urethritis are recognized, based on the causative agent: gonococcal urethritis (GU) and non-gonococcal urethritis (NGU). GU is due to a *Neisseria gonorrhoeae* infection, while NGU may be caused by one or more of: *Chlamydia trachomatis, Ureaplasma urealyticum, Mycoplasma hominis, Mycoplasma genitalium*, or *Trichomonas vaginalis*. Co-infections by *Neisseria gonorrhoeae* and *Chlamydia trachomatis* are also seen. The common occurrence of recurrent infection and the emergence of antimicrobial resistance in the pathogens causing urethritis demonstrate the need for a single, broadly active drug for management of this STD (Centers for Disease Control and Prevention. Increases in fluoroquinolone-resistant *Neisseria gonorrhoeae*-Hawaii and California, 2001. *Morbidity Mortality Weekly Rpt.* 51: 1041-1044 (2002); Centers for Disease Control and Prevention. Update to CDC's sexually transmitted diseases treatment guidelines, "Fluoroquinolones no longer recommended for treatment of gonococcal infections." *Morbidity Mortality Weekly Rpt.* 56: 332-336 (2006); Merchant et al., *Int. J. STD AIDS* 20:534-539 (2009); Palmer et al., *J. Antimicrob. Chemother.* 62:490-494 (2008); Roberts et al., *Antimicrob. Agents Chemother.* 43:1367-1372 (1999); Roblin et al., *Antimicrob. Agents Chemother.* 42:194-196 (1998)). Because of sexual practices, two of the bacterial species associated with urethritis, namely *Neisseria gonorrhoeae* and *Chlamydia trachomatis*, can also cause infections of the throat, and passage through the birth canal can cause infections in infants. Trachoma conjunctivitis in children is a leading cause of blindness in the world (Burton et al., The global burden of trachoma: a review. *PLoS Negl Trop Dis.* 3(10):e460 (2009)). Therefore, drugs effective in the treatment of urethritis would also be expected to have efficacy in the treatment of ocular and pharyngeal infections caused by *Neisseria gonorrhoeae* and/or *Chlamydia trachomatis*.

Fusidic acid (FA) is a tetracyclic triterpenoid or fusidane (steroidal) antibiotic derived from the fungus *Fusidium coccineum* that inhibits bacterial protein synthesis. FA is effective against gram-positive bacteria such as *Staphylococcus* species and *Corynebacterium* species (L. Verbist, *J. Antimicro. Chemo.* 25, Suppl. B, 1-5 (1990); A. Bryskier, Fusidic Acid, Chapter 23, in *Antimicrobial Agents: Antibacterials and Antifungals* (Andre Bryskier, Ed., ASM Press, Washington, USA, 2005)). FA also has moderate activity against Group A beta-hemolytic streptococci, including *Streptococcus pyogenes* (L. Verbist, *J. Antimicro. Chemo.* 25, Suppl. B, 1-5 (1990); A. Bryskier, Fusidic Acid, Chapter 23, in *Antimicrobial Agents: Antibacterials and Antifungals* (Andre Bryskier, Ed., ASM Press, Washington, USA, 2005); Skov et al., *Diag. Micro. Infect. Dis.* 40:111-116 (2001)).

FA was developed for clinical use in the 1960s and it is approved for human use outside of the United States, such as in the UK, Canada, Europe, Israel, Australia and New Zealand. It is typically prescribed at doses of 500 mg TID for treating skin and skin structure infections caused by *Staphylococcus aureus* (A. Bryskier, Fusidic Acid, Chapter 23, in *Antimicrobial Agents: Antibacterials and Antifungals* (Andre Bryskier, Ed., ASM Press, Washington, USA, 2005); Collignon et al., *Int'l J. Antimicrobial Agents* 12:S45-S58 (1999); D. Spelman, *Int'l J. Antimicrobial Agents* 12:S59-S66 (1999)), although some physicians have routinely prescribed the compound at 500 mg BID for treating skin and skin structure infections due to the long half-life of the compound (Fusidic Acid, in *Principles and Practice of Infectious Diseases, 6th* ed. (Mandell et al. eds., Elsevier, 2006)).

Treatment using FA has been well studied and it is generally regarded as safe when administered to humans, as evidenced by the fact that the drug has been in continuous use since 1968 in various parts of the world. There are, however, several characteristics of FA that have suggested against the use of the drug against a wider spectrum of bacteria and in the treatment in additional types of infection. For example, approved dosing regimens have been shown to select for bacterial resistance, such as in *S. aureus*. Approved dosing regimens provide low multiples of the MIC and as a result, *S. aureus* resistant mutants can be selected after the first day of dosing. Once resistance has developed, FA is not effective against the resistant strains. Resistance is reported to occur if FA is used as a single drug as the resistance frequency at 4 and 8 times the MIC is in the range of $10^{-6}$ or $10^{-8}$ (Evans et al., *J. Clin. Path.* 19:555-560 (1966); Hansson et al., *J. Mol. Biol.* 348:939-949 (2005), Jensen et al., *Acta Pathol Microbiol Scand.* 60:271-284 (1964); Besier et al., *Antimicrob. Agents Chemo.,* 49(4):1426-1431 (2005); Gemmell et al., *J. Antimicrobial Chemo.* 57:589-608 (2006); Howden et al., *Clin. Infect. Disease* 42:394-400 (2006)).

The dosage of the drug cannot be simply increased as a means of avoiding development of resistance. It is difficult to achieve high concentrations of free (unbound) FA in the blood due to the substantial protein binding of the drug (approximately 95-97%) (K. Christiansen, International Journal of Antimicrobial Agents 12:S3-S9 (1999); Coutant et al., *Diagn Microbiol Infect Dis* 25:9-13 (1996); D. Reeves, *J. Antimicrob. Chemo.* 20:467-476 (1987); J. Turnidge, *Int'l J. Antimicrobial Agents* 12:S23-S34 (1999); Rieutord et al., *Int'l J. Pharmaceutics* 119:57-64 (1995)). Moreover, high dosages of FA are not well-tolerated by patients receiving the drug. High doses of FA (e.g., 1 gram TID) are required if the drug is to be used in the treatment of bone and joint infections, less susceptible bacteria and other serious infections. However, treatment regimens using high doses of the drug induce nausea and vomiting and are rejected by patients (Fusidic Acid, in *Principles and Practice of Infectious Diseases, 6th* ed. (Mandell et al. eds., Elsevier, 2006); K. Christiansen, International Journal of Antimicrobial Agents 12:S3-S9 (1999); Nordin et al., *Eur. J. Clin. Res.* 5:97-106 (1994)).

In view of the tremendous costs associated with the de novo development of new anti-bacterials, expanding the indications for drugs that have already been demonstrated to be safe and effective is strongly needed. Finding new uses and means for administering FA would broaden the population of bacterial infections against which FA could be used and thus meet this need.

BRIEF SUMMARY OF THE INVENTION

The present invention is directed to methods of treating or preventing a bacterial infection in a subject, comprising administering a therapeutically effective amount of a pharmaceutical composition comprising fusidic acid, or a pharmaceutically acceptable salt thereof, to a subject in need of treatment or prevention, wherein the bacterial infection is caused by *Neisseria gonorrhoeae, Chlamydia trachomatis*, or both *Neisseria gonorrhoeae* and *Chlamydia trachomatis*.

In certain aspects, the bacterial infection is urethritis, an ocular infection, or a pharyngeal infection.

In certain preferred aspects, the pharmaceutical composition is administered to the subject once or twice over the entire course of treatment or prevention, wherein the entire course of treatment or prevention is about 12 hours or less. In such aspects, the therapeutically effective amount of the pharmaceutical composition comprises between about 3000 mg and 4000 mg fusidic acid, or a pharmaceutically acceptable salt thereof, whether administered in one dose or BID.

In other preferred aspects, the pharmaceutical composition is administered to the subject once or twice daily over the entire course of treatment or prevention. In such aspects, the therapeutically effective amount of the pharmaceutical composition administered on the first day is between about 3000 mg and 4000 mg fusidic acid, or a pharmaceutically acceptable salt thereof, whether administered in one dose or BID, and the therapeutically effective amount of the pharmaceutical composition administered on subsequent days is between about 2000 and 2800 mg fusidic acid, or a pharmaceutically acceptable salt thereof, whether administered in one dose or BID.

In preferred aspects of the invention, the subject is a human.

In preferred aspects of the invention, the pharmaceutical composition comprising fusidic acid, or a pharmaceutically acceptable salt thereof, is a pharmaceutical composition in the form of a tablet, a capsule, or a solution.

In preferred aspects of the invention, the subject does not experience dose-limiting nausea or vomiting after administration of the pharmaceutical composition.

The present invention is also directed to the use of fusidic acid, or a pharmaceutically acceptable salt thereof, in the manufacture of a medicament for the treatment, or prevention, or both, of a bacterial infection caused by *Neisseria gonorrhoeae, Chlamydia trachomatis*, or both, in a subject. In certain aspects, the bacterial infection is urethritis, an ocular infection, or a pharyngeal infection.

The invention is further directed to fusidic acid, or a pharmaceutically acceptable salt thereof, for use in the treatment, or prevention, or both, of a bacterial infection caused by *Neisseria gonorrhoeae, Chlamydia trachomatis*, or both. In certain aspects, the bacterial infection is urethritis, an ocular infection, or a pharyngeal infection.

DETAILED DESCRIPTION OF THE INVENTION

Through numerous studies and the diligent efforts of the inventors, and as disclosed herein, it has been discovered that bacterial infections caused by *Neisseria gonorrhoeae* and *Chlamydia trachomatis* can be successfully treated using fusidic acid. As such, the present invention provides methods for the treatment and prevention of bacterial infections caused by *Neisseria gonorrhoeae, Chlamydia trachomatis* or both *Neisseria gonorrhoeae* and *Chlamydia trachomatis*, using fusidic acid, or a pharmaceutically acceptable salt thereof. The methods of the present invention may be practiced by administering to a subject a pharmaceutical composition comprising fusidic acid, or a pharmaceutically acceptable salt thereof, as disclosed herein.

The present invention is thus directed to methods of treating or preventing a bacterial infection in a subject, comprising administering a therapeutically effective amount of a pharmaceutical composition comprising fusidic acid, or a pharmaceutically acceptable salt thereof, to a subject in need of treatment or prevention, wherein the bacterial infection is caused by *Neisseria gonorrhoeae, Chlamydia trachomatis*, or both *Neisseria gonorrhoeae* and *Chlamydia trachomatis*. In certain aspects, the bacterial infection is urethritis, an ocular infection, or a pharyngeal infection.

The therapeutically effective amount of a pharmaceutical composition and the amounts sufficient to achieve the stated goals of the methods disclosed herein will vary depending upon the physical characteristics of the subject, the severity of the subject's symptoms, the identity of the bacteria, the location of the bacterial infection, the formulation and the means used to administer the drug, the number of doses being administered to the subject over the course of treatment or prevention, and the method being practiced. The specific dose for a given subject is usually set by the judgment of the attending physician.

In one aspect of the invention, complete treatment or prevention is achieved by administering the pharmaceutical composition over a period of less than about 24 hours, preferably less than about 18, 15, 12 or 9 hours. In this aspect, a therapeutically effective amount of a pharmaceutical composition of the present invention will typically comprise between about 2000 mg and about 4000 mg, or a value within this range, of fusidic acid, or a pharmaceutically acceptable salt thereof, preferably between about 3000 mg and about 4000 mg, or a value within this range, regardless of the formulation. Particular therapeutically effective amounts of the pharmaceutical composition may comprise 2000, 2100, 2200, 2300, 2400, 2500, 2600, 2700, 2800, 2900, 3000, 3100, 3200, 3300, 3400, 3500, 3600, 3700, 3800, 3900, or 4000 mg, or more, when the pharmaceutical composition is administered over a period of less than about 24 hours. The pharmaceutical composition is preferably administered in one dose, but it may also be divided into two, three, four or more doses, all of which are administered within about 24 hours. For example, a single dose of 3000 mg may be administered to a subject, or two 1500 mg doses may be administered to the subject about 12 hours apart.

In a second aspect of the invention, treatment or prevention is achieved by administering the pharmaceutical composition over several days. In this aspect, a therapeutically effective amount of a pharmaceutical composition of the present invention will typically comprise between about 1000 mg and about 4000 mg, or a value within this range, of fusidic acid, or a pharmaceutically acceptable salt thereof, preferably between about 3000 mg and about 4000 mg, or a value within this range, and administered on the first day of treatment or prevention. Subsequent doses administered on succeeding days will typically comprise between about 1500 mg and about 3500 mg, or a value within this range, of fusidic acid or a pharmaceutically acceptable salt thereof, preferably between about 2000 mg and about 2800 mg, or a value within this range, Particular therapeutically effective amounts of the pharmaceutical composition administered on the first day may comprise 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg. The pharmaceutical composition is preferably administered in one dose, but it may also be divided into two, three, four or more doses, all of which are administered within the first day. Particular therapeutically effective amounts of the pharmaceutical composition administered on succeeding days may comprise 1500, 1600, 1700, 1800, 1900, 2000, 2100, 2200, 2300, 2400, 2500, 2600, 2700, 2800, 2900, 3000, 3100, 3200, 3300, 3400, or 3500 mg. The pharmaceutical composition is preferably administered in one dose, but it may also be divided into two, three, four or more doses, all of which are administered within each succeeding day of treatment or prevention. The number of days required to complete the course of treatment or prevention will vary, but includes 1, 2, 3, 4, 5, 6, 7, 8, 9, 10 or more days.

In each of the embodiments of the present invention, the following common aspects and preferred common aspects are encompassed within the scope of the invention.

Fusidic Acid (FA) has the following structure.

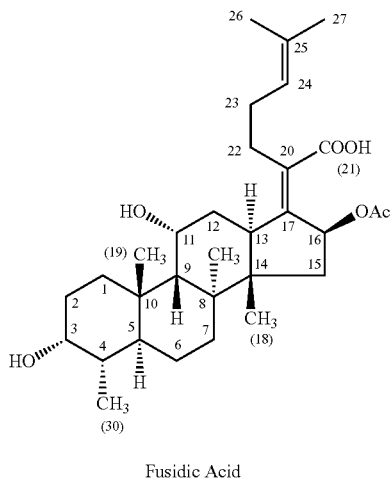

Fusidic Acid

The skilled artisan will understand that for the sake of brevity alone, all references herein to "fusidic acid" or "FA", unless otherwise stated, also refers to the hemihydrate form of the compound, as well as pharmaceutically acceptable salts, other hydrates, solvates, or mixtures thereof.

The term "pharmaceutically acceptable salt" refers to nontoxic base addition salts derived from inorganic and organic bases. Base addition salts include those derived from inorganic bases, such as ammonium or alkali or alkaline earth metal hydroxides, carbonates, bicarbonates, and the like, as well as alkylamine and organic amino salts, such as an ethanolamine salt. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred. In preferred embodiments, sodium fusidate is a pharmaceutically acceptable salt that is used in the methods of the present invention. Sodium fusidate, also termed CEM-102 herein, has the following structure.

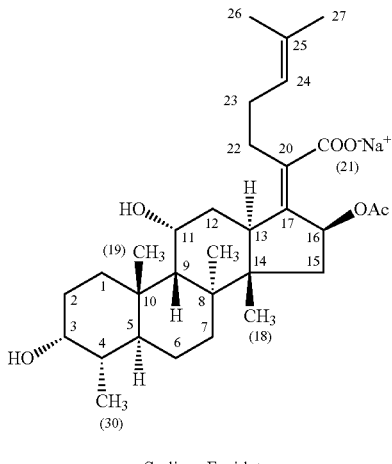

Sodium Fusidate

It should be recognized that the particular counter-ion forming a part of any salt of this invention is not of a critical nature, so long as the salt as a whole is pharmacologically acceptable and as long as the counter-ion does not contribute undesired qualities to the salt as a whole.

In each of the embodiments of the present invention, the subject being subjected to treatment or prevention is a human. The subject may have a bacterial infection, such as where the present invention is directed to methods for treating a bacterial infection caused by *Neisseria gonorrhoeae, Chlamydia trachomatis*, or both *Neisseria gonorrhoeae* and *Chlamydia trachomatis*, such as urethritis, an ocular infection or a pharyngeal infection caused by one or both of these organisms. The subject may also be at risk for developing a bacterial infection, such as where the present invention is directed to methods for preventing a bacterial infection caused by *Neisseria gonorrhoeae, Chlamydia trachomatis*, or both *Neisseria gonorrhoeae* and *Chlamydia trachomatis*, such as urethritis, an ocular infection or a pharyngeal infection caused by one or both of these organisms.

The embodiments of the present invention may be used to treat a bacterial infection when the causative agent(s) has been identified, i.e., an infection caused by one or both of *Neisseria gonorrhoeae* and *Chlamydia trachomatis*. The embodiments of the present invention may also be used to treat a bacterial infection, such as urethritis, an ocular infection or a pharyngeal infection, when the causative agent(s) has not been identified, but is reasonably suspected of being one or both of *Neisseria gonorrhoeae* and *Chlamydia trachomatis*. The embodiments of the present invention may further be used prophylactically to prevent a bacterial infection prior to exposure, such as in the sexual partner of a subject diagnosed with urethritis, an ocular infection or a pharyngeal infection caused by one or both of *Neisseria gonorrhoeae* and *Chlamydia trachomatis*, or thought to be caused by one or both of these organisms.

While the present invention is directed to the treatment or prevention of bacterial infections, such as urethritis, ocular infections and pharyngeal infections caused by one or both of *Neisseria gonorrhoeae* and *Chlamydia trachomatis*, the methods of the present invention may be used to treat or prevent infections caused by these organisms occurring in any other area of a subject's body. Such infections include: conjunctivitis, pharyngitis, proctitis, prostatitis, orchitis, endocarditis, meningitis, dermatitis-arthritis syndrome, and pelvic inflammatory disease caused by *Neisseria gonorrhoeae*, and proctitis, trachoma, infertility, prostatitis, epididymitis, cervicitis, pelvic inflammatory disease, ectopic pregnancy, and acute or chronic pelvic pain caused by *Chlamydia trachomatis*.

In each of the embodiments of the present invention, the fusidic acid may be administered to a subject in conjunction with a second therapeutic agent, such as a second antibiotic. The second therapeutic agent may be administered before, concurrent with or after administration of the fusidic acid, whether in the same formulation or in a separate formulation. Suitable second therapeutic agents include rifampin, rifamycin, a sulfonamide, a beta-lactam, a tetracycline, a chloramphenicol, an aminoglycoside, a macrolide, a streptogramin, a quinolone, a fluoroquinolone, an oxazolidinone and a lipopeptide. In particular, tetracycline, tetracycline derived antibacterial agents, glycylcycline, glycylcycline derived antibacterial agents, minocycline, minocycline derived antibacterial agents, oxazolidinone antibacterial agents, aminoglycoside antibacterial agents, quinolone antibacterial agents, vancomycin, vancomycin derived antibacterial agents, teicoplanin, teicoplanin derived antibacterial agents, eremomycin, eremomycin derived antibacterial agents, chloroeremomycin, chloroeremomycin derived antibacterial agents, daptomycin, and daptomycin derived antibacterial agents are preferred. In a preferred aspect of the embodiments, rifampin is administered concurrently with the fusidic acid.

In each of the embodiments of the present invention, the subject does not experience dose-limiting nausea and dose-limiting vomiting over the entire course of treatment or prevention.

The pharmaceutical compositions of the present invention comprise fusidic acid, a hemihydrate form thereof, or pharmaceutically acceptable salts, other hydrates, solvates, or mixtures thereof, and one or more of a carrier, diluent and excipient. The terms specifically exclude cell culture medium. Suitable diluents (for both dry and liquid pharmaceutical formulations) are well known to those skilled in the art and include saline, buffered saline, dextrose (e.g., 5% dextrose in water), water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717).

Carriers are compounds and substances that improve and/or prolong the delivery of an active ingredient to a subject in the context of a pharmaceutical formulation. Carrier may serve to prolong the in vivo activity of a drug or slow the release of the drug in a subject, using controlled-release technologies. Carriers may also decrease drug metabolism in a subject and/or reduce the toxicity of the drug. Carrier can also be used to target the delivery of the drug to particular cells or tissues in a subject. Common carriers (both hydrophilic and hydrophobic carriers) include fat emulsions, lipids, PEGylated phospholipids, liposomes and liposheres, microspheres (including those made of biodegradable polymers or albumin), polymer matrices, biocompatible polymers, protein-DNA complexes, protein conjugates, erythrocytes, vesicles and particles.

Excipients included in a pharmaceutical composition have different purposes depending, for example on the nature of the drug, and the mode of administration. Examples of generally used excipients include, without limitation: stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

In particular, the pharmaceutical compositions may contain common carriers and excipients, such as microcrystalline cellulose, crospovidone, hypromellose, lactose monohydrate, magnesium stearate, silica, all-rac-α-tocopherol, talc and titanium dioxide.

The particular carrier, diluent or excipient used will depend upon the means and purpose for which the active ingredient is being applied.

The pharmaceutical compositions of the present invention may be formulated for oral or ocular administration. The unit dosage of the pharmaceutical composition can be in a concentrated liquid, powder or granular form for ex tempore reconstitution in the appropriate pharmaceutically acceptable carrier, such as sterile water, at the time of delivery.

For oral use, the oral pharmaceutical composition may be made in the form of a unit dosage containing a therapeutically effective amount of the pharmaceutical composition. Solid formulations such as tablets and capsules are particularly useful. Sustained released or enterically coated preparations may also be devised. For pediatric and geriatric applications, suspension, syrups, slow release and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to fusidic acid, inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavoring (e.g. peppermint, oil of wintergreen, fruit flavoring, cherry, grape, bubblegum, and the like), and coloring agents. The tablets and capsules may also include coating excipients such as glyceryl monostearate or glyceryl distearate, to delay absorption in the gastrointestinal tract.

In a particular oral formulation, the pharmaceutical compositions of the present invention may be in the form of a tablet containing microcrystalline cellulose, crospovidone, hypromellose, lactose monohydrate, magnesium stearate, silica, all-rac-α-tocopherol, talc and titanium dioxide, and optionally one or more other inactive ingredients. Suitable amounts of fusidic acid in a tablet may range from about 10 to about 4000 mg, or a value within this range, with preferred amounts including about 250, 300, 350, 400, 450, 500, 550, 600, 650, 700, 750, 800, 850, 900, 950, or 1000 mg of fusidic acid per tablet.

Oral liquid preparations, generally in the form of aqueous or oily solutions, suspensions, emulsions or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, microcrystalline cellulose, methyl or propyl para-hydroxybenzoate, propylene glycol, sorbitol, or sorbic acid. In a particular oral formulation, the pharmaceutical composition comprises fusidic acid and the following inactive ingredients:

acesulfame potassium, flavor, citric acid, disodium phosphate dihydrate, hydroxyethylcellulose, glucose liquid, methylcellulose, sodium benzoate, sorbitol, and purified water. Suitable amounts of fusidic acid in an oral formulation may range from about 10 to about 4000 mg, or a value within this range, with preferred amounts including about 250, 300, 350, 400, 450, 500, 550, 600, 650, 700, 750, 800, 850, 900, 950, or 1000 mg of fusidic acid in the oral formulation.

For ocular use, an eye drop solution is prepared comprising fusidic acid. In one embodiment, the ocular formulation comprises fusidic acid and the following inactive ingredients: benzalkonium chloride, disodium edetate, mannitol, carbomer, sodium hydroxide, and water. Suitable amounts of fusidic acid in an eye drop formulation may range from about 1 to about 100 mg, or a value within this range, with preferred amounts including about 5, 10, 15, 20, 25, 30, 35, 40, 45, 50, 55, 60, 65, 70, 75, 80, 85, 90, 95, or 100 mg of fusidic acid in the formulation.

As used herein, the terms "dose", "dosage", "unit dose", "unit dosage", "effective dose" and related terms refer to physically discrete units that contain a predetermined quantity of active ingredient calculated to produce a desired therapeutic effect. These terms are synonymous with the therapeutically effective amounts and amounts sufficient to achieve the stated goals of the methods disclosed herein.

As used herein, the terms "treating" and "treatment" have their ordinary and customary meanings, and include one or more of, ameliorating a symptom of urethritis in a subject, blocking or ameliorating a recurrence of a symptom of urethritis in a subject, decreasing in severity and/or frequency a symptom of urethritis in a subject, stasis, decreasing, or inhibiting growth of bacteria causing urethritis in a subject, and killing bacteria causing urethritis in a subject. Treatment means ameliorating, blocking, reducing, decreasing or inhibiting by about 1% to about 100% versus a subject to which a pharmaceutical composition has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition has not been administered.

As used herein, the terms "preventing" and "prevention" have their ordinary and customary meanings, and include one or more of preventing bacteria causing urethritis from colonizing a subject, preventing an increase in the growth of a bacterial population causing urethritis in a subject, preventing development of urethritis caused by a bacterial infection in a subject, and preventing symptoms of urethritis caused by a bacterial infection in a subject. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 0.5, 1, 2, 3, 4, 5, 6, 7, 8, 9, 10, 12, 14, 16, 18, 20, 25, 30, 35, 40, 45, 50 or more days after administration of a pharmaceutical composition.

EXAMPLES

Example 1

In Vitro Activity of CEM 102 Against *Chlamydia trachomatis*

*Chlamydia trachomatis* is the most prevalent sexually transmitted infection in the United States today. In vitro activity of macrolide and ketolide antibiotics against *C. trachomatis* varies, with clarithromycin showing the lowest MICs followed by, azithromycin and doxycycline. The in vitro activities of CEM 102 was compared with those of azithromycin, clarithromycin, telithromycin and doxycycline against 10 strains of *C. trachomatis*.

Antibiotics: CEM 102, telithromycin, azithromycin, clarithromycin, and doxycycline were provided as powders and solubilized according to the instructions of the manufacturers. Drug suspensions were made fresh each time the assay was run.

*Chlamydia* isolates: 10 isolates of *C. trachomatis* in order to determine the $MIC_{90}$ and $MBC_{90}$ for each antibiotic.

*C. trachomatis*: 10 isolates of *C. trachomatis*, including standard isolates from the ATCC (E-BOUR, F-IC-CAL3, C-HAR32, J-UW-36, L2434, D-UW-57kx, B-HAR-36) and recent clinical isolates N18 (cervical), N19 (cervical), 7015 (infant eye).

In vitro susceptibility testing: Susceptibility testing of *C. trachomatis* was performed in cell culture using HEp-2 cells grown in 96-well microtiter plates. Each well was inoculated with 0.1 ml of the test strain diluted to yield $10^3$ to $10^4$ IFU/per ml, centrifuged at 1,700×g for 1 hr and incubated at 35° C. for 1 hr. Wells were then aspirated and overlaid with 0.2 ml of medium containing 1 µg of cycloheximide per ml and serial two fold dilutions of the test drug. Duplicate plates were inoculated. After incubation at 35° C. for 48-72 hrs, cultures were fixed and stained for inclusions with fluorescein-conjugated antibody to the lipopolysaccharide genus antigen (PATHFINDER™, Kallestad Diagnostics, Chaska, Minn.). The minimal inhibitory concentration (MIC) was the lowest antibiotic concentration at which no inclusions are seen. The minimal bactericidal concentration (MBC) was determined by aspirating the antibiotic containing medium, washing wells twice with phosphate buffered saline and adding antibiotic-free medium. Cultures were frozen at −70° C., thawed, passed onto new cells, incubated for 72 hrs then fixed and stained as above. The MBC was the lowest antibiotic concentration that results in no inclusions after passage. All tests were run in triplicate.

The activity of CEM 102 against 10 strains of *C. trachomatis* is shown in Table 1.

TABLE 1

| Strain | MIC (µg/ml) | MBC (µg/ml) |
| --- | --- | --- |
| Ct H | 0.5 | 0.5 |
| Ct E | 0.5 | 0.5 |
| Ct F | 0.5 | 0.5 |
| 7015 | 0.5 | 0.5 |
| Ct I | 0.5 | 0.5 |
| N18 | 0.25 | 0.25 |
| Ct D | 0.5 | 0.5 |
| Ct J | 0.5 | 0.5 |
| L2 | 0.25 | 0.25 |
| N19 | 0.125 | 0.125 |

$MIC_{90}$ 0.5 µg/ml
$MBC_{90}$ 0.5 µg/ml

Example 2

Fusidic Acid (CEM-102) Tested Against *Neisseria gonorrhoeae* and *Chlamydia trachomatis*

Thirty-five clinical isolates of *N. gonorrhoeae* collected in the United States (USA), Asia and European medical centers since 2005 were tested using reference agar dilution methods per Clinical and Laboratory Standards Institute (CLSI) M07-

A8 (Clinical and Laboratory Standards Institute. 2009. M07-A8, Methods for dilution antimicrobial susceptibility tests for bacteria that grow aerobically; approved standard—eighth edition. Wayne, Pa.: CLSI) and M100-S20 documents (Clinical and Laboratory Standards Institute. 2010. M100-S20, Performance standards for antimicrobial susceptibility testing, 20th informational supplement. Wayne, Pa.: CLSI). Five strains were penicillinase-positive, and all gonococci were identified to species level by at least two laboratories including a reference, central laboratory (JMI Laboratories, North Liberty, Iowa, USA). Resistance phenotypes were determined by agar dilution test results followed by confirmatory techniques as required by CLSI M100-S20 criteria (Clinical and Laboratory Standards Institute. 2010. M100-S20, Performance standards for antimicrobial susceptibility testing, 20th informational supplement. Wayne, Pa.: CLSI). Quality control (QC) ranges and interpretive criteria for comparator compounds were as published by CLSI (Clinical and Laboratory Standards Institute. 2010. M100-S20, Performance standards for antimicrobial susceptibility testing, 20th informational supplement. Wayne, Pa.: CLSI). Tested QC strains included *Staphylococcus aureus* ATCC 29213, *Enterococcus faecalis* ATCC 29212 and *N. gonorrhoeae* ATCC 49226 with all results being within established limits.

The activities of fusidic acid and five comparators tested against *N. gonorrhoeae* are shown in Table 2. Resistance rates for this organism collection were: penicillin (45.7%), tetracycline (34.3%), ciprofloxacin (20.0%), ceftriaxone (0.0%) and azithromycin (0.0%). The $MIC_{90}$ of fusidic acid against these *N. gonorrhoeae* was only 1 µg/ml. Using $MIC_{50}$ (0.5 µg/ml) results, fusidic acid was two-fold more active than penicillin and tetracycline ($MIC_{50}$, 1 µg/ml), but slightly less potent than azithromycin (0.25 µg/ml). Fusidic acid was active against all strains of *N. gonorrhoeae* strains tested at ≦2 µg/ml.

Ten isolates of *C. trachomatis* including standard isolates from the ATCC (E-BOUR, F-IC-CAL3, C-HAR32, J-UW-36, L2434, D-UW-57kx, B-HAR-36) and recent clinical isolates N18 (cervical), N19 (cervical), 7015 (infant eye) were selected for study. Susceptibility testing was performed in cell culture using HEp-2 cells (Roblin et. al. *Antimicrob. Agents Chemother.* 42:194-196 (1998)) at State University of New York, Downstate Medical Center (Brooklyn, N.Y., USA).

The activity of fusidic acid against *C. trachomatis* was compared with those of azithromycin, clarithromycin, telithromycin and doxycycline (Table 3). The MIC range of fusidic acid against *C. trachomatis* was 0.12-0.5 µg/ml with an identical fusidic acid $MBC_{90}$ and $MIC_{90}$ for this organism of 0.5 µg/ml. The $MIC_{90}$ values for azithromycin, clarithromycin, telithromycin and doxycycline were 0.12, 0.06, 0.06 and 0.06 µg/ml, respectively; each two- to four-fold lower than fusidic acid.

These in vitro testing data suggest that fusidic acid may be considered as an alternative treatment for multidrug-resistant *N. gonorrhoeae* strains and could provide an advantage for treatment of STD as a single agent targeting both gonococcus and *C. trachomatis* (Adimora, A. A. *Clin. Infect. Dis.* 35: Suppl S2, 183-186 (2002); Centers for Disease Control and Prevention. 2006. Update to CDC's sexually transmitted diseases treatment guidelines, "Fluoroquinolones no longer recommended for treatment of gonococcal infections." *Morbidity and Mortality Weekly Rep.* 56: 332-336 (2006); Creighton et al., *Int. J. STD AIDS* 14:109-113 (2003); Merchant et al., *Int. J. STD AIDS* 20:534-539 (2009)). The pharmacokinetics of fusidic acid has been recently modeled to define safe high-dose regimens designed to attenuate selection of resistance that was reported for doses originally approved for clinical use in Europe and Australia, as well as to maximize potency versus cutaneous infection pathogens such as *Staphylococcus aureus* (Olanrewaju et al., CEM-102 (Sodium Fusidate) dosage regimen decision support using population pharmacokinetic (PPK) and mechanism-based pharmacokinetic-pharmacodynamic (PK-PD) models, abstr. A-1141. 47th Ann. Meet. Infec. Dis. Soc. Am. Infectious Diseases Society of America, Philadelphia, Pa. (2009); Still et al., Pharmacokinetics and safety of single, multiple, and loading doses of CEM-102 in healthy subjects, abstr. A-1528. 49th Intersci. Conf. Antimicrob. Agents and Chemother., San Francisco, Calif. (2009)). These modified dosing schedules achieve fusidic acid trough plasma levels of ca. 80 ug/ml, representing 40 to 160-fold greater concentrations than the highest *N. gonorrhoeae* or *C trachomatis* MIC result found in this report (Godtfredsen et al., *The Lancet* 279: 928-931 (1962); Olanrewaju et al., CEM-102 (Sodium Fusidate) dosage regimen decision support using population pharmacokinetic (PPK) and mechanism-based pharmacokinetic-pharmacodynamic (PK-PD) models, abstr. A-1141. 47th Ann. Meet. Infec. Dis. Soc. Am. Infectious Diseases Society of America, Philadelphia, Pa. (2009); Still et al., Pharmacokinetics and safety of single, multiple, and loading doses of CEM-102 in healthy subjects, abstr. A-1528. 49th Intersci. Conf. Antimicrob. Agents and Chemother., San Francisco, Calif. (2009)).

TABLE 2

Activity of fusidic acid and five comparator agents tested against a comprehensive resistant challenge collection of contemporary *N. gonorrhoeae* isolates (35 strains).

| Antimicrobial | Occurrences at MIC (µg/ml): | | | | | | | | | | | % by category[a] |
| --- | --- | --- | --- | --- | --- | --- | --- | --- | --- | --- | --- | --- |
| | ≦0.008 | 0.015 | 0.03 | 0.06 | 0.12 | 0.25 | 0.5 | 1 | 2 | 4 | >4 | S/R |
| Fusidic acid | — | — | — | — | — | 12 | 17 | 5 | 1 | — | — | —[b]/— |
| Azithromycin | — | — | — | 1 | 15 | 12 | 5 | 1 | 1 | — | — | —/— |
| Ceftriaxone | 18 | 6 | 6 | 3 | 2 | — | — | — | — | — | — | 100.0/— |
| Ciprofloxacin | 16 | 2 | — | — | 5 | 3 | 2 | 1 | 1 | — | 5 | 51.4/20.0 |
| Penicillin | — | 1 | 4 | 3 | — | 2 | 4 | 5 | 6 | 4 | 6 | 22.9/45.7 |
| Tetracycline | — | — | — | — | 6 | 2 | 8 | 7 | 7 | 1 | 4 | 22.9/34.3 |

[a]CLSI criteria (Clinical and Laboratory Standards Institute. 2010. M100-S20, Performance standards for antimicrobial susceptibility testing, 20th informational supplement. Wayne, PA: CLSI). S = susceptible and R = resistant.
[b]— = no interpretive criteria.

TABLE 3

Activity of fusidic acid and four comparator agents tested against *C. trachomatis* (10 strains)

| Antimicrobial | MIC (µg/mL)[a] | | MBC (µg/mL)[b] | |
|---|---|---|---|---|
| | Range | 90% | Range | 90% |
| Fusidic acid | 0.12-0.5 | 0.5 | 0.12-0.5 | 0.5 |
| Azithromycin | 0.015-0.12 | 0.12 | 0.015-0.12 | 0.12 |
| Clarithromycin | 0.015-0.12 | 0.06 | 0.015-0.12 | 0.06 |
| Telithromycin | 0.015-0.25 | 0.06 | 0.015-0.25 | 0.06 |
| Doxycycline | 0.015-0.06 | 0.06 | 0.015-0.06 | 0.06 |

[a]Minimum inhibitory concentration (MIC); defined as the lowest antimicrobial concentration at which no intracellular inclusions were observed
[b]Minimum bactericidal concentration (MBC); defined as the lowest antimicrobial concentration that results in no observable inclusions after passage in cell culture All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

What is claimed is:

1. A method of treating a bacterial infection in a subject, comprising administering a therapeutically effective amount of a pharmaceutical composition comprising fusidic acid, or a pharmaceutically acceptable salt thereof, to a subject in need of treatment, wherein the bacterial infection is caused by *Chlamydia trachomatis* or both *Neisseria gonorrhoeae* and *Chlamydia trachomatis*.

2. The method of claim 1, wherein the bacterial infection is urethritis, an ocular infection, or a pharyngeal infection.

3. The method of claim 1, wherein the entire course of treatment is about 12 hours or less, and wherein the therapeutically effective amount of the pharmaceutical composition comprises between about 3000 mg and about 4000 mg of fusidic acid, or a pharmaceutically acceptable salt thereof.

4. The method of claim 1, wherein between about 3000 mg and about 4000 mg of fusidic acid, or a pharmaceutically acceptable salt thereof, is administered to the subject on the first day of treatment, and wherein between about 2000 mg and about 2800 mg of fusidic acid, or a pharmaceutically acceptable salt thereof, is administered to the subject on succeeding days of treatment.

5. The method of claim 3, wherein the pharmaceutical composition is administered QD or BID.

6. The method of claim 4, wherein the administration is independently QD or BID on each day of treatment.

7. The method of claim 1, wherein the subject is a human.

8. The method of claim 1, wherein the pharmaceutical composition is a tablet, a capsule, or a solution.

9. The method of claim 1, wherein the pharmaceutical composition is administered orally or ocularly.

10. The method of claim 1, wherein a second therapeutic agent is administered to the subject in addition to the pharmaceutical composition.

11. The method of claim 10, wherein the second therapeutic agent is rifampin.

12. A method of treating urethritis in a subject, comprising administering a therapeutically effective amount of a pharmaceutical composition comprising fusidic acid, or a pharmaceutically acceptable salt thereof, to a subject in need of treatment.

13. The method of claim 12, wherein the entire course of treatment is about 12 hours or less, and wherein the therapeutically effective amount of the pharmaceutical composition comprises between about 3000 mg and about 4000 mg of fusidic acid, or a pharmaceutically acceptable salt thereof.

14. The method of claim 12, wherein between about 3000 mg and about 4000 mg of fusidic acid, or a pharmaceutically acceptable salt thereof, is administered to the subject on the first day of treatment, and wherein between about 2000 mg and about 2800 mg of fusidic acid, or a pharmaceutically acceptable salt thereof, is administered to the subject on succeeding days of treatment.

15. The method of claim 13, wherein the pharmaceutical composition is administered QD or BID.

16. The method of claim 14, wherein the administration is independently QD or BID on each day of treatment.

17. The method of claim 12, wherein the subject is a human.

18. The method of claim 12, wherein the pharmaceutical composition is a tablet or a capsule.

19. The method of claim 12, wherein a second therapeutic agent is administered to the subject in addition to the pharmaceutical composition.

20. The method of claim 19, wherein the second therapeutic agent is rifampin.

* * * * *